United States Patent
Wrobel et al.

(10) Patent No.: US 7,377,645 B2
(45) Date of Patent: May 27, 2008

(54) ARRANGEMENT AND METHOD FOR ILLUMINATING THE LENS OF THE HUMAN EYE

(75) Inventors: Walter Wrobel, Jena (DE); Ingo Koschmieder, Jena (DE); Karl-Heinz Donnerhacke, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 439 days.

(21) Appl. No.: 10/501,020

(22) PCT Filed: Jan. 9, 2003

(86) PCT No.: PCT/EP03/00129

§ 371 (c)(1),
(2), (4) Date: Jan. 3, 2005

(87) PCT Pub. No.: WO03/057023

PCT Pub. Date: Jul. 17, 2003

(65) Prior Publication Data

US 2005/0107708 A1    May 19, 2005

(30) Foreign Application Priority Data

Jan. 10, 2002    (DE)    ................ 102 00 718

(51) Int. Cl.
  *A61B 3/10*    (2006.01)
  *A61B 3/00*    (2006.01)
  *A61B 6/00*    (2006.01)

(52) U.S. Cl. ............. 351/221; 351/200; 351/205; 600/476; 606/6; 359/368

(58) Field of Classification Search ........... 351/200, 351/201, 203, 206, 208–212, 214, 219, 221, 351/243, 245, 246, 272, 160 R; 600/401, 600/407, 476, 544, 545; 348/42, 47, 51, 348/54; 345/6, 8, 419, 757; 362/105, 257, 362/268; 359/290, 298, 618, 368
See application file for complete search history.

(56) References Cited

U.S. PATENT DOCUMENTS 5,202,708 A    4/1993    Sasaki et al. ........... 351/206

(Continued)

FOREIGN PATENT DOCUMENTS

DE    197 27 573    5/1998

(Continued)

*Primary Examiner*—Loha Ben
(74) *Attorney, Agent, or Firm*—Reed Smith LLP

(57) ABSTRACT

The present invention is directed to an arrangement for generating a variable illumination and irradiation for diagnosis and therapy, particularly for the human eye (1), and to a method for the application thereof. The object to be illuminated can be an artificial object or biological tissue. The arrangement for carrying out the illumination/irradiation of a human eye (1) comprises an illumination unit (2, 3), an optical imaging system (4), an evaluating unit, a central control unit (6) and an output unit (7). The illumination unit (2, 3) generates an illumination which is variable with respect to time and/or space and which is adapted to the diagnostic results. The solution according to the invention is provided chiefly for post-operative fine adjustment of the refractive power of photosensitive plastics already implanted in the eye (1). The latter can be optical lenses as well as other optical elements which are placed in a specific manner in the cornea. However, application of the invention for achieving dermatological effects is also conceivable.

25 Claims, 3 Drawing Sheets

U.S. PATENT DOCUMENTS

| | | | |
|---|---|---|---|
| 5,784,146 A | 7/1998 | Nanjo et al. | 351/214 |
| 6,038,067 A * | 3/2000 | George | 359/368 |
| 6,086,204 A | 7/2000 | Magnanate | 351/212 |
| 6,275,718 B1 | 8/2001 | Lempert | 600/407 |
| 6,315,412 B1 * | 11/2001 | Snodderly et al. | 351/200 |
| 6,423,001 B1 * | 7/2002 | Abreu | 600/405 |

FOREIGN PATENT DOCUMENTS

| | | |
|---|---|---|
| DE | 198 12 050 | 9/1999 |
| DE | 199 43 735 | 5/2001 |
| DE | 101 51 314 | 4/2003 |
| DE | 101 55 464 | 5/2003 |
| WO | WO 00/41650 | 7/2000 |
| WO | WO 01/71411 | 9/2001 |
| WO | WO 02/26121 | 4/2002 |
| WO | WO 02/31576 | 4/2002 |

* cited by examiner

ARRANGEMENT AND METHOD FOR ILLUMINATING THE LENS OF THE HUMAN EYE

CROSS-REFERENCE TO RELATED APPLICATIONS

This application claims priority of International Application No. PCT/EP03/00129, filed Jan. 9, 2003 and German Application No. 102 00 718.7, filed Jan. 10, 2002, the complete disclosures of which are hereby incorporated by reference.

BACKGROUND OF THE INVENTION a) Field of the Invention

The present invention is directed to an arrangement for generating a variable illumination and irradiation for diagnosis and therapy, particularly for the human eye, and to a method for the application thereof. The object illuminated by the variable illumination can be an artificial object or biological tissue. However, with respect to the eye, it is also possible to irradiate other parts of the eye besides the lens, such as the cornea, retina or fundus. In particular, the invention can be used for fine adjustment of photosensitive plastics introduced into the eye (according to WO 00/41650 and WO 01/71411). With plastics of this type, the irradiation excites polymerization processes that result in irreversible chemical changes in the substance. The index of refraction, geometric shape and/or transmission behavior for the visible useful radiation and the geometric shape of the plastic body can be changed in a defined manner by these processes. In this way, it is possible to improve defective vision.

b) Description of the Related Art

Patents WO 00/41650 and WO 01/71411 describe lenses, particularly intraocular lenses (IOL) in which polymerization of a polymer matrix contained in the lens is excited by irradiation and the index of refraction or the shape of the entire lens can be changed in this way. With implanted IOLs, the problem exists that in approximately 50% of patients an acceptable visual acuity can be achieved only through additional corrective measures such as eyeglasses or contact lenses. This is the result, in part, of errors in eye measurements, deviations in the positioning of the IOL and/or is due to the healing process. With the described IOLs, a correction of the IOL which is already implanted is made possible through directed irradiation by adapting to the actual conditions through changes in the index of refraction, the transmission characteristics or the optically active shape. The irradiation of the IOL for exciting the polymerization process is preferably effected by means of laser sources or lamps emitting a high UV component of the light. For this purpose, an He/Cd laser or an Xe/Hg lamp is used as the irradiation source. Illumination structures which may possibly be required are generally produced by means of mechanical diaphragms and/or filters.

However, there are disadvantages to arrangements of the kind described above in that the supply of patterns is limited by fixed diaphragms, there is no possibility of intensity distribution within the diaphragm patterns, and dynamic processes can be realized, at best, through manual switching and, therefore, hardly at all. Moreover, the generated illumination patterns can not be adapted to individual findings and are not adaptive or suitable for online regulation.

199 43 735 A1 describes a method and a device for directed irradiation of an eye by means of light from the UV-A and/or visible near infrared wavelength range. The irradiation brings about irreversible chemical changes in the eye lens substance which result in a change in the index of refraction and/or in the transmission characteristics for the visible useful radiation and which accordingly make it possible to improve defective vision. Successful treatment requires that the distribution of the refractive power of the eye being treated is determined over the most closely-knit, fullest area possible. The refractive power distribution desired after treatment and the data for the irradiation that are required for this purpose are determined from these values. Inevitably, however, the eyeball must usually be fixated for the duration of the treatment.

Patents WO 02/26121 and WO 02/31576 describe solutions for the irradiation of optical lenses or lens systems made from photosensitive plastics (according to WO 00/41650 and WO 01/71411) which are already implanted in the eye as intraocular lenses. In this solution, the irradiation patterns in question are determined by a computer program based on a wavefront analysis that is carried out beforehand. In addition to a diagnostic element for monitoring before, during and after irradiation, a surgical microscope is provided for additional visual observation. However, this solution has disadvantageous results in that there is only one fixating light for the patient. Experience has shown that it is difficult for the patient to concentrate on a stationary fixating light for the duration of treatment, so that movements of the eye can nevertheless occur.

DE 198 12 050 A1 describes a method and an arrangement for illumination in an ophthalmic microscope. A large variety of light mark geometries is generated by means of optoelectronic components and projected on the anterior portion or on the fundus of the eye. This solution is used for general examination of the eye. An arrangement for generating section images in transparent media is provided in DE 101 55 464.8, which has not yet been published. An ophthalmological examination device which enables a perimetric examination as well as a general eye examination has also not been published (DE 101 51 314.3). The solutions contained in both of these references likewise provide for the use of optoelectronic components for generating illumination marks and illumination patterns.

OBJECT AND SUMMARY OF THE INVENTION

It is the primary object of the present invention to develop a method and an arrangement for illumination and irradiation of a human eye for therapeutic purposes and for correcting the characteristics of photosensitive plastics already implanted in the eye. An optimized visual acuity is adjusted in the patient by means of this correction, so that additional aids such as eyeglasses or contact lenses need not be worn.

According to the invention, this object is met by an arrangement for the illumination/irradiation of a human eye, particularly of photosensitive, optically active plastics implanted in the eye, comprising an illumination unit, an optical imaging system, an evaluating unit, a central control unit and an output unit. The illumination unit generates an illumination which is variable with respect to time and/or space.

The proposed technical solution substantially comprises the illumination unit and an optical imaging system and can be used as an independent unit or as an accessory unit for different ophthalmological devices such as slit lamps, fundus cameras, laser scanners and OPMI devices. This results in a broad range of applications that is not limited only to the field of ophthalmology. The irradiation unit can also be used as an accessory unit for various dermatological irradiation devices in order to bring about a specific effect through directed irradiation with variable illumination.

The invention will be described in the following with reference to embodiment examples.

DESCRIPTION OF THE PREFERRED EMBODIMENTS

Figure 1:
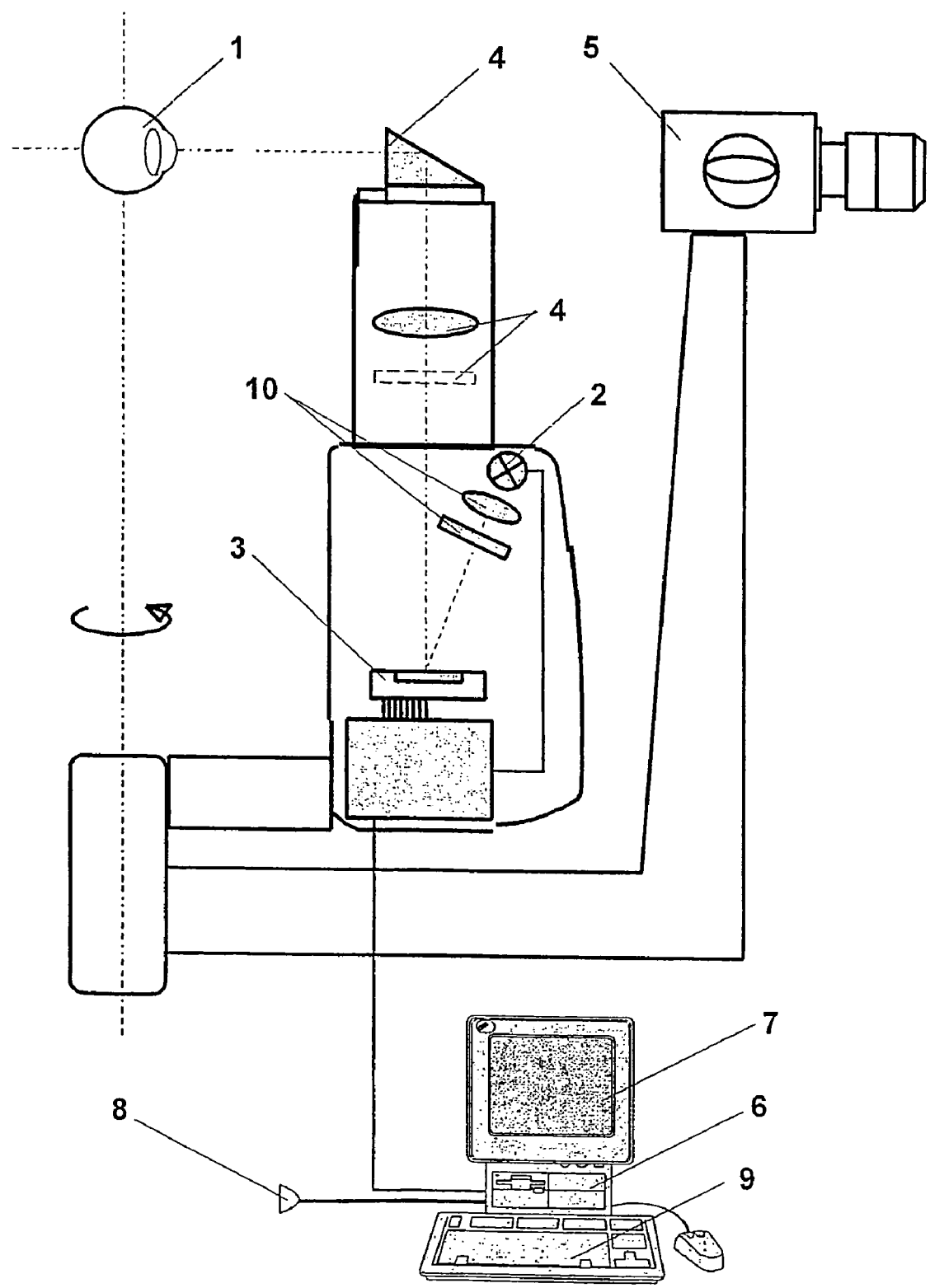
FIG. 1 shows a possible basic construction of the arrangement according to the invention with a DMD microdisplay.

FIG. 1 shows the basic construction of the arrangement according to the invention for generating an illumination which is variable with respect to time and/or space for diagnosis and therapy, particularly of the human eye 1.

The arrangement substantially comprises an illumination unit, an optical imaging system 4, an evaluating unit, a central control unit 6 and an output unit 7. The illumination unit comprises an illumination source 2 and an optoelectronic component 3. The illumination source 2 is controllable with respect to its intensity and duration and, for this purpose, possesses additional means for controlling and monitoring the emitted light. A lamp or laser source which is controllable with respect to the spectral composition of the light bundle is used as illumination source 2. The control of the spectral composition can be carried out by means of a filter wheel (not shown). A DMD (digital micromirror device) microdisplay is used as optoelectronic component 3. In order to ensure a uniform illumination, a light conducting fiber, a glass mixing rod, an integrator rod, or a suitable condenser arrangement 10 is used for transmitting the light beam from the illumination source to the microdisplay. The provided optical imaging system 4 has an adjustable numerical aperture and a variable back focus for sharp imaging of the illumination pattern in different planes of the object space. In this way, different illumination patterns can be generated along the optical axis in different planes of the object, e.g., on the front surface of the lens or back surface of the lens, and geometric-spatial effects can accordingly be produced. This possibility of imaging the illumination patterns in different planes can advantageously be combined with a distance control and/or a focusing aid for the eye. In this way, the position along the optical axis can also be accurately adjusted and maintained constant. The focusing aid can be carried out based on the principle of multiple spot imaging using a high aperture in which all of the individual spots coincide only in the target plane and result in one individual spot. A distance control can be carried out, for example, by means of known four-quadrant receivers which evaluate the vertex reflection of the cornea. The variably adjustable numerical aperture can be used to regulate the intensity of the illumination pattern in the imaging plane on the one hand and, on the other hand, to maintain the current limit values for the illumination in the eye by influencing the beam density at the retina.

By combining the adjustable aperture diaphragm with the function of the adjustable back focus or focal length and the realization of dynamic illumination patterns, specific irradiation sequences with special patterns can be realized at determined locations with continuous monitoring of the permissible radiation dose. Position control and position correction are carried out by means of an eyetracker unit and ensure an exact illumination only in the aligned focused state even during eye movements, so that mechanical fixation of the patient's eye can be dispensed with.

Further, an observation system 5 and an evaluating unit are provided for measurement, evaluation, documentation and readout. The evaluating unit comprises an image-recording unit and a processing unit. The central control unit 6 for input, acquisition, processing and storage of data has a user surface 9 and an interface 8. A monitor, a printer and/or a HMD (head mounted display), for example, are used as output unit 7 for visualization and readout of data.

Figure 2:
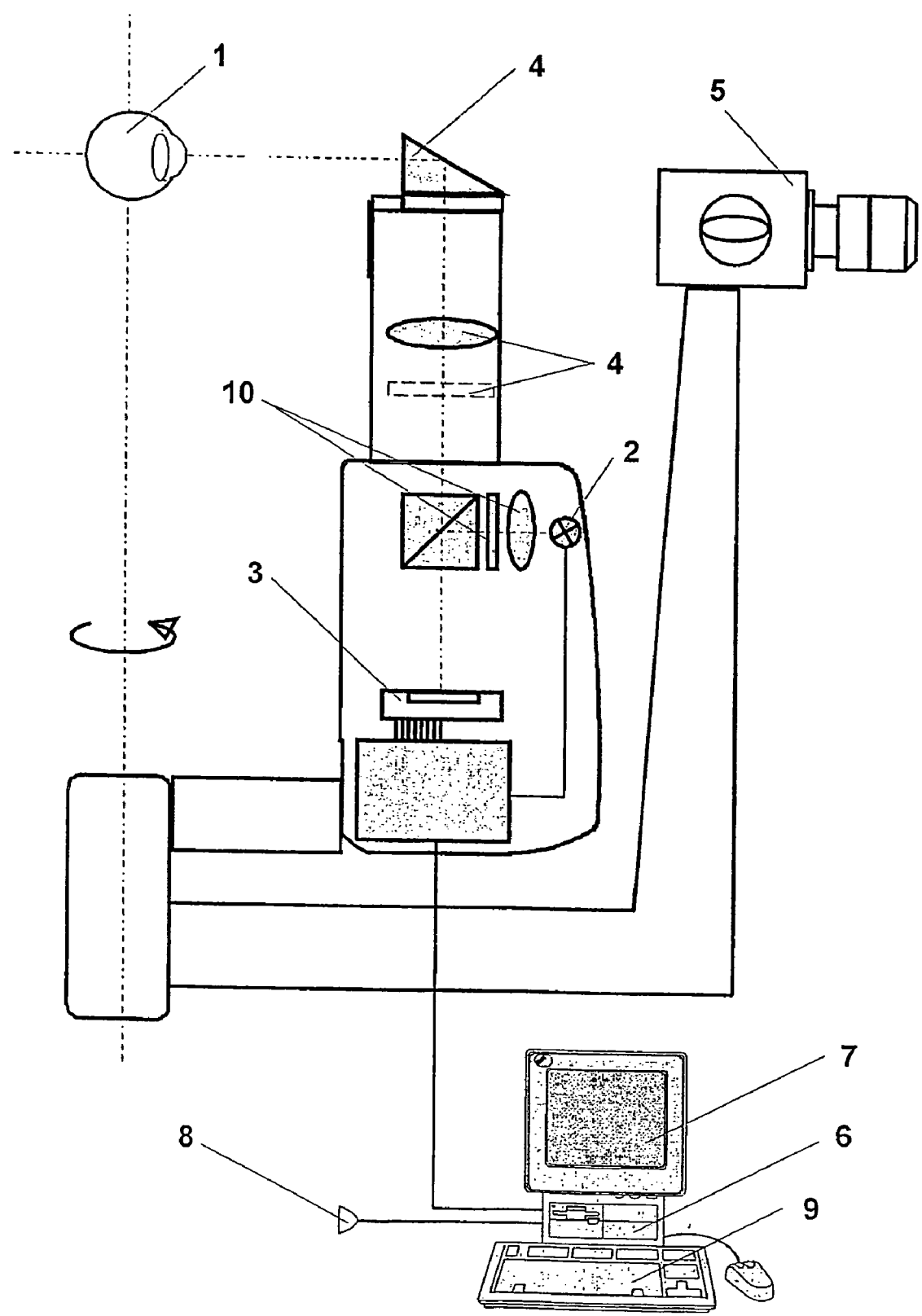
FIG. 2 shows another possible basic construction of the arrangement according to the invention with a LCOS microdisplay.

In contrast, FIG. 2 shows the basic construction of the arrangement according to the invention for generating structured illumination in which a LCOS (liquid crystal on silicon) reflecting microdisplay is used as optoelectronic component 3 instead of a DMD microdisplay. However, transmissive LCD (liquid crystal display), self-luminous LED (light emitting diode) or OLED (organic light emitting diode) optoelectronic components 3 can also be used. In the basic construction shown in FIG. 1, a microscanning mirror with two individually controllable oscillation planes could also be used instead of the microdisplay.

In the method for generating illumination which is variable with respect to time and/or space particularly when operating one of the arrangements described above, after the findings or result data that were determined beforehand (refraction state) have been entered from the central control unit 7, the parameters of the illumination radiation which are required for the intended purpose are determined and conveyed to the illumination source 2 and the optoelectronic component 3. Based on the determined data, static or dynamic irradiation patterns geared to the specific application can be generated for directed spatial and temporal sequences.

The method is suitable particularly for illumination/irradiation of optical lenses or other elements already implanted in the eye. These elements comprise photosensitive base materials according to Patents WO 00/41650 and WO 01/71411 so that their optical-mechanical characteristics can be changed within a certain time period by stimulation with light.

Apart from intraocular lenses (IOL), the plastic lenses to be illuminated can be, in particular, anterior chamber lenses (e.g., Artisan lenses and Nuvita lenses) or intraocular contact lenses (ICL).

However, there are also other optical elements such as intercorneal rings, as they are called, which can be placed in the cornea in a specific manner and cause a change in the refractive conditions of the cornea due to their shape and position. Implantation is relatively conservative for the patient because neither the epithelium nor the endothelium are damaged or altered except for a peripheral entry point (mounting opening). These intercorneal rings are placed in the cornea in a specific manner and, due to their shape and position, cause a tightening of the surface of the cornea to varying extents and accordingly change the refractive conditions of the cornea. Since the method is not necessarily limited to the ring structure, differently shaped elements such as thin disks are also possible.

Figure 3:
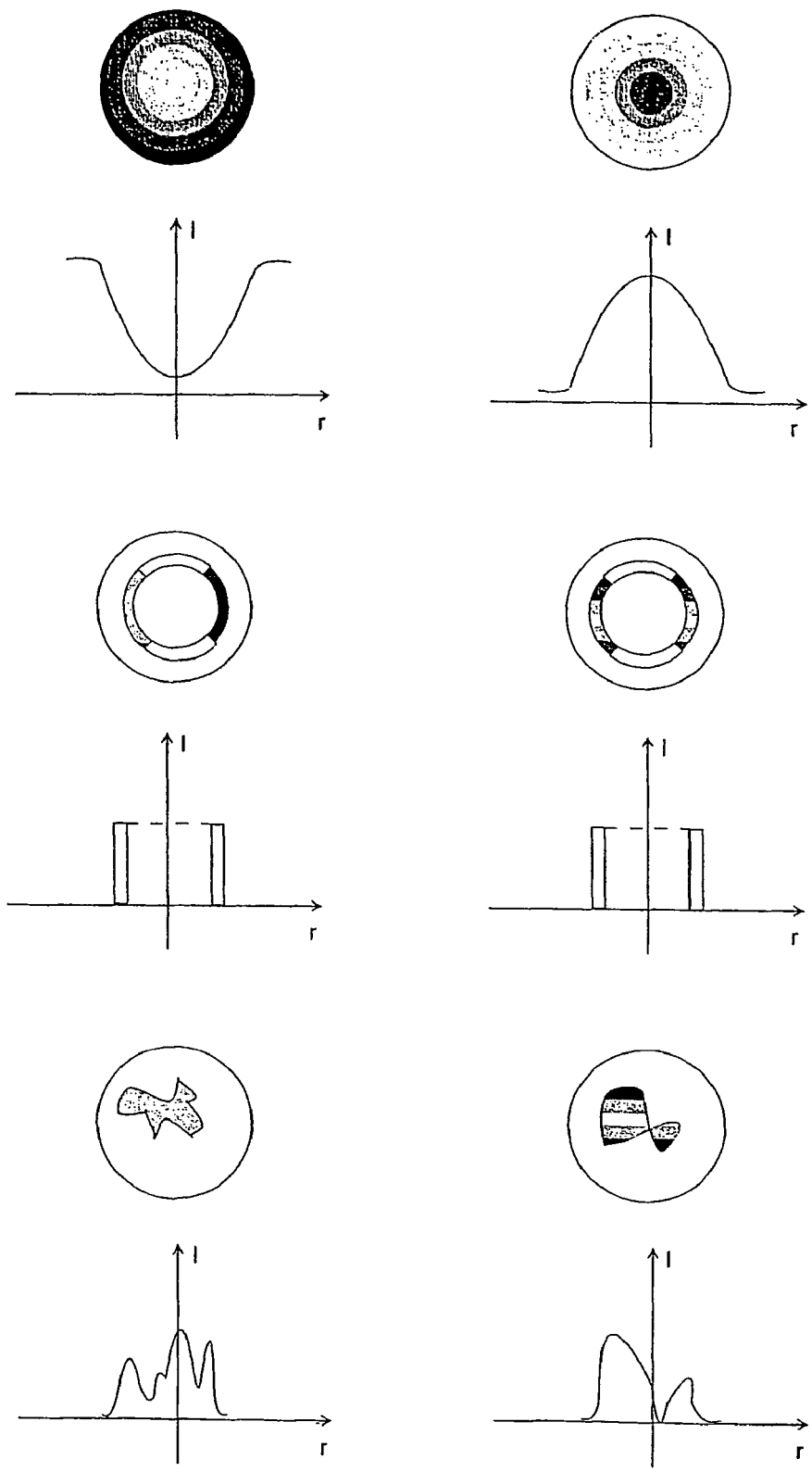
FIG. 3 shows possible illumination patterns with the associated intensity distribution.

FIG. 3 shows possible irradiation patterns and the associated intensity distributions. Result data may come from preliminary examinations with appropriate measuring instruments or can be determined within the device itself. In this connection, possible result data may include results of a wavefront analysis and data from topography examinations. It is even useful and conceivable to combine the data from different examinations. The result data can be transferred by entering them manually through the user surface 9 or, more conveniently, by transferring the data via the interface 8. The irradiation pattern generated by the illumination source 2 and the optoelectronic component 3 is imaged in the object space by the imaging system 4 in a plane which is freely adjustable within certain limits. The observation system 5 is used for visually monitoring and observing the eye 1 during the irradiation process. For purposes of automated image evaluation and in order to enable online control, the corresponding measured values are supplied to the evaluating unit by an image-recording and processing unit. For recording, processing, documentation and evaluation, the recorded images and data are further processed, logged and stored by the central control unit 6. An output unit 7 documents the evaluation results.

The use of an eyetracker unit comprising a camera and an IR illumination is particularly advantageous. The eyetracker unit can be coupled in, e.g., by a beam splitter, monitors possible eye movements and checks whether or not the generated illumination patterns strike exactly the areas of the eye or of the photosensitive plastic to be irradiated. When the illumination pattern exceeds, radially or laterally, a certain tolerance value that is determined beforehand for a time period that is likewise determined beforehand, the irradiation is interrupted and only continues after the target state has been reached again. The duration of the irradiation is evaluated in order to ensure the respective dose and to match it to the desired preset values. The tolerance is selected depending on the required accuracy for reaching the reference state.

When tolerances that were determined beforehand are exceeded radially or laterally, the illumination pattern can deliberately follow the eye movement. This is advantageous in that the irradiation process need not be interrupted. In order to steady the patient's eye, a luminous fixating mark can be projected on the eye. This light mark should advantageously blink and should be presented to the patient optically from infinity in order to make it possible to see and recognize the mark in a relaxed manner. In this connection, it is possible to project the fixating mark on the eye to be treated or on the other eye which is not to be treated. However, the fixating mark can also be used for deliberate positioning of the patient's eye in certain directions. For this purpose, another microdisplay can advantageously be used in which the position of the mark can be shifted optoelectronically without moving parts.

The tracking of the illumination pattern on the eye can likewise be carried out in an advantageous manner without any moving parts in that the pattern is simply displaced close in time on the optoelectronic component corresponding to the scaled preset of the eyetracker unit.

The illumination for the camera of the eyetracker unit should be carried out in a spectral range other than that of the observation wavelength and treatment wavelength. This prevents reciprocal influencing of the beam paths. The use of an eyetracker unit with IR illumination and corresponding tracking of the pattern is especially advantageous when particularly finely structured illumination patterns are to be used for higher aberration refraction correction.

For purposes of visual monitoring, it is possible to display the target field, tolerance field and tracking field in the observation unit. This is carried out by reflecting into the eyepiece or by imaging in a plane conjugate to the target object in which a corresponding display is located.

Irradiation, e.g., for polymerization of artificial eye lenses, requires illumination sources 2 having a high UV component such as mercury arc lamps, xenon lamps or UHP lamps. However, because of this high UV component of the light, particular attention must be paid to the permissible radiation load corresponding to current guidelines, and steps may have to be taken for specific attenuation of harmful components, e.g., by means of suitable edge filters. The irradiation unit which comprises the illumination source 2 and the optoelectronic component 3 and which is constructed as an independent unit in this example can be used as an accessory unit for various ophthalmological instruments such as slit lamps, fundus cameras, laser scanners and OPMI devices in order to generate illumination structures or irradiation structures with a defined dosage. However, the irradiation unit can also be used as an accessory unit or as an independent device for different dermatological irradiation devices.

The solution according to the invention is chiefly provided for post-operative fine adjustment of the refractive power of photosensitive plastics already implanted in the eye. These photosensitive plastics can be optical lenses as well as other optical elements which are placed in the cornea in a specific manner and which cause a change in the refraction relationships of the cornea through their shape and position.

Since it is possible to adapt to individual result data, other fields of application are opened up by the possibility of realizing dynamic processes and online regulation. For example, combined determination of initial data, i.e., of the refraction state, in the form of wavefront analyses and corneal topography is possible. During exposure, the eyetracker unit can be used for monitoring the position and for tracking the pattern on the eye to improve the process of positioning or tracking the illumination pattern also during long irradiation times of several seconds. It is even possible to determine the refraction state online during treatment depending on the achieved processing state of the object to be illuminated.

By means of directed beam deflection within the lens or by means of other optically active shaped parts, the image center or determined points of the imaging could be deflected onto other areas of the receiver. This is useful, for example, when the patient's retina is severely damaged by scotomas in determined areas which can no longer contribute to visual perception. Through specific individual alteration of the local refractive power within the lens, the imaging can be shifted to healthy areas of the retina.

Further, application in photodynamic therapy is also possible. In this way, progressive diseases of the macula which could not be halted previously can now be stopped even in the visual center through a novel laser procedure by irradiation of a newly developed dye.

However, application for achieving dermatological results in which determined effects can be produced by the introduction or addition of light-sensitive materials and subsequent structured irradiation is also conceivable.

While the foregoing description and drawings represent the present invention, it will be obvious to those skilled in the art that various changes may be made therein without departing from the true spirit and scope of the present invention.

The invention claimed is:

1. An arrangement for an illumination/irradiation of a human eye, particularly of photosensitive, optically active plastics implanted in the eye, comprising:
   an illumination unit for illuminating the active plastics;
   an optical imaging system responsive to the illumination unit for imaging data on measured values of the active plastics;
   an evaluating unit responsive to the measured values;
   a central control unit for acquiring and entering said data; and
   an output unit for visualization and readout of said data;
   said illumination unit for generating an illumination which is variable with respect to time and/or space.

2. The arrangement for the illumination/irradiation of a human eye according to claim 1, wherein the illumination unit comprises an illumination source and an optoelectronic component.

3. The arrangement for the illumination/irradiation of a human eye according to claim 2, wherein a microdisplay or a microscanner mirror is used as said optoelectronic component which is controllable with respect to light transmission, light reflection or light emission.

4. The arrangement for the illumination/irradiation of a human eye according to claim 1, wherein the central control unit is used for further processing and storing said data and has a user surface and an interface.

5. The arrangement for the illumination/irradiation of a human eye according to claim 1, wherein the evaluating unit comprises an image-recording and image-processing unit.

6. The arrangement for the illumination/irradiation of a human eye according to claim 1, wherein a monitor, a printer and/or a HMD (head mounted display) are used as said output unit for the visualization and readout of said data.

7. The arrangement for the illumination/irradiation of a human eye according to claim 1, wherein the optical imaging system has an adjustable numerical aperture and/or a variable back focus or focal length for sharp imaging of the illumination pattern in different planes.

8. The arrangement for the illumination/irradiation of a human eye according to claim 1, wherein a self-luminous array is used instead of the illumination unit.

9. The arrangement for the illumination/irradiation of a human eye according to claim 1, wherein an eyetracker unit is provided and comprises a camera and a preferably infrared illumination which is coupled in, for example, by means of a beam splitter.

10. The arrangement for the illumination/irradiation of a human eye according to claim 1, wherein a fixating mark is additionally projected on the eye to be treated or on the other eye which is not to be treated, this fixating mark being formed as a blinking light mark which is presented optically from infinity and/or is adjustable to the refraction state of the patient.

11. The arrangement for the illumination/irradiation of a human eye according to claim 1, wherein the arrangement is used for the illumination of photosensitive plastics already implanted in the eye, in particular intercorneal rings.

12. The arrangement for the illumination/irradiation of a human eye according to claim 1, wherein a fixating/mark is additionally projected on the eye to be treated or on the other eye which is not to be treated, this fixating mark being formed as a blinking light mark which is presented optically from infinity and is freely adjustable with respect to its attitude and position.

13. A device for the illumination/irradiation of a human eye according to claim 1, wherein the illumination unit which comprises an illumination source and an optoelectronic component is constructed as an independent unit which can be used as an accessory unit for various ophthalmological instruments comprising slit lamps, fundus cameras, laser scanners and OPMI devices in order to generate illumination structures or irradiation structures with a defined dosage.

14. The device for illumination/irradiation according to claim 1, wherein the illumination unit which comprises an illumination source and an optoelectronic component is constructed as an independent unit which can be used as an accessory unit for various dermatological irradiation instruments in order to generate illumination structures or irradiation structures with a defined dosage.

15. A method for an illumination/irradiation of a human eye, particularly when operating an arrangement comprising an illumination unit for illuminating the eye, an optical imaging system responsive to the illuminating unit for imaging data on measured values of the eye, an evaluating unit responsive to the measured values a central control unit for processing and storing data, and an output unit for visualization and readout of said data; the method including the steps of generating an illumination by the illumination unit which is variable with respect to time and/or space, and applying said illumination to photosensitive, optically active plastics implanted in the eye.

16. The method for the illumination/irradiation of a human eye according to claim 15, further comprising the steps of entering the result data which have been determined beforehand manually or by transferring the data via an existing interface or through a decision by the arrangement itself.

17. The method for the illumination/irradiation of a human eye according to claim 15, including the step of imaging the irradiation pattern generated by the illumination unit, comprising an illumination source and an optoelectronic component, by the imaging system in a freely adjustable object plane.

18. The method for the illumination/irradiation of a human eye according to claim 15, wherein an automatic image evaluation and/or online control are/is made possible based on the measured values determined by the evaluating unit.

19. The method for the illumination/irradiation of a human eye according to claim 15, including storing determined data for recording, documentation and evaluation.

20. The method for the illumination/irradiation of a human eye according to claim 15, wherein evaluation results are documented by the output unit.

21. The method for the illumination/irradiation of a human eye according to claim 15, wherein static or dynamic irradiation patterns geared to a specific application can be generated for directed spatial and temporal sequences.

22. The method for the illumination/irradiation of a human eye according to claim 15, wherein parameters which are required for an intended purpose are determined on the basis of these data by the central control unit and conveyed to the illumination unit.

23. The method for the illumination/irradiation of a human eye according to claim 15, wherein an eyetracker checks whether or not generated illumination patterns strike exactly areas of the eye or of a photosensitive plastic to be irradiated during the irradiation.

24. The method for the illumination/irradiation of a human eye according to claim 15, wherein generated illumination patterns track a possible eye movement by an eyetracker unit and the illumination unit.

25. The method for the illumination/irradiation of a human eye according to claim 15, wherein a generated illumination pattern is used for the illumination of said photosensitive plastics already implanted in the eye, in particular intercorneal rings.

* * * * *